United States Patent
Tao et al.

(10) Patent No.: US 10,849,653 B2
(45) Date of Patent: Dec. 1, 2020

(54) THERMOFORM CANNULA WITH VARIABLE CANNULA BODY STIFFNESS

(71) Applicant: Abiomed, Inc., Danvers, MA (US)

(72) Inventors: Zhenghong Tao, Winchester, MA (US); Christopher Zarins, Boston, MA (US); Dion Mraz, Arlington, VA (US); Stephen Vaughan, Medford, MA (US); Julius Steven Becker, Andover, MA (US)

(73) Assignee: ABIOMED, INC., Danvers, MA (US)

( * ) Notice: Subject to any disclaimer, the term of this patent is extended or adjusted under 35 U.S.C. 154(b) by 0 days.

(21) Appl. No.: 15/419,203

(22) Filed: Jan. 30, 2017

(65) Prior Publication Data
US 2017/0215918 A1  Aug. 3, 2017

Related U.S. Application Data

(60) Provisional application No. 62/288,914, filed on Jan. 29, 2016.

(51) Int. Cl.
| | | |
|---|---|---|
| *A61M 1/12* | (2006.01) | |
| *A61B 17/34* | (2006.01) | |
| *A61M 1/10* | (2006.01) | |
| A61M 25/00 | (2006.01) | |
| A61B 17/00 | (2006.01) | |

(52) U.S. Cl.
CPC ...... *A61B 17/3423* (2013.01); *A61B 17/3439* (2013.01); *A61B 17/3468* (2013.01); *A61M 1/101* (2013.01); *A61M 1/1008* (2014.02); *A61M 1/1029* (2014.02); *A61M 1/122* (2014.02); *A61M 1/125* (2014.02); *A61B 2017/00955* (2013.01); *A61B 2017/3425* (2013.01); *A61M 25/005* (2013.01); *A61M 25/0045* (2013.01); *A61M 25/0054* (2013.01)

(58) Field of Classification Search
None
See application file for complete search history.

(56) References Cited

U.S. PATENT DOCUMENTS

| | | | |
|---|---|---|---|
| 6,007,478 A | * | 12/1999 | Siess ................. A61M 25/0053 600/16 |
| 6,264,645 B1 | | 7/2001 | Jonkman |
| 6,544,216 B1 | | 4/2003 | Sammler et al. |

(Continued)

FOREIGN PATENT DOCUMENTS

WO  2016034171 A2  3/2016

OTHER PUBLICATIONS

ISR (PCTUS2017/15574) dated Apr. 28, 2017.
Supplementary European Search Report EP 17 74 5072 dated Jul. 12, 2019.

*Primary Examiner* — Erica S Lee
(74) *Attorney, Agent, or Firm* — Botis Churchill IP Law LLP

(57) ABSTRACT

A cannula supporting a percutaneous pump can include a proximal section with a first flexural modulus. The cannula can include one or more distal sections with a flexural modulus that is different than the first flexural modulus. The material and its arrangement along the length of the cannula can be selected so as to influence bending properties. This can, for example, allow efficient positioning of the cannula in a desired location without displacing the guidewire.

21 Claims, 7 Drawing Sheets

(56) References Cited

U.S. PATENT DOCUMENTS

| | | | |
|---|---|---|---|
| 6,673,040 B1 * | 1/2004 | Samson | A61B 17/12022 604/101.01 |
| 2004/0158206 A1 | 8/2004 | Kboul-Hosn et al. | |
| 2006/0004346 A1 | 1/2006 | Begg | |
| 2006/0063965 A1 * | 3/2006 | Aboul-Hosn | A61M 25/0043 600/16 |
| 2007/0156010 A1 * | 7/2007 | Aboul-Hosn | A61M 1/3653 600/18 |
| 2007/0197856 A1 * | 8/2007 | Gellman | A61M 1/3653 600/16 |
| 2010/0268017 A1 | 10/2010 | Siess | |
| 2013/0253328 A1 | 9/2013 | Zelenka et al. | |
| 2014/0107399 A1 * | 4/2014 | Spence | A61M 1/1008 600/16 |
| 2014/0155862 A1 * | 6/2014 | Baxter | A61B 17/22 604/508 |
| 2015/0038770 A1 * | 2/2015 | Colella | A61M 1/122 600/16 |
| 2015/0080743 A1 | 3/2015 | Siess | |
| 2015/0328382 A1 * | 11/2015 | Corbett | A61M 1/122 600/16 |

\* cited by examiner

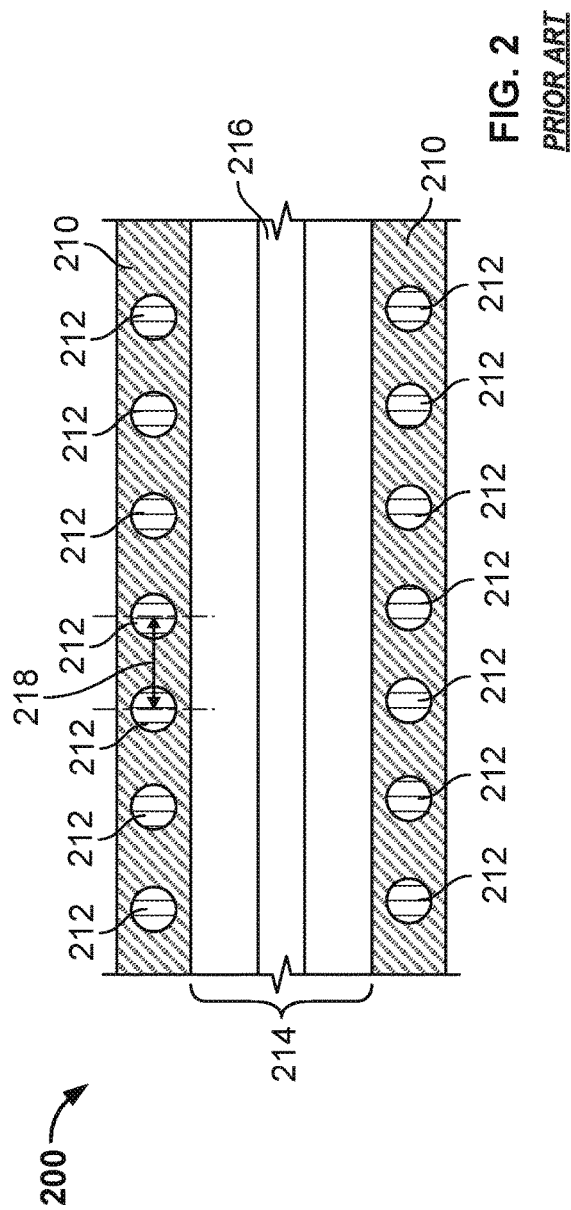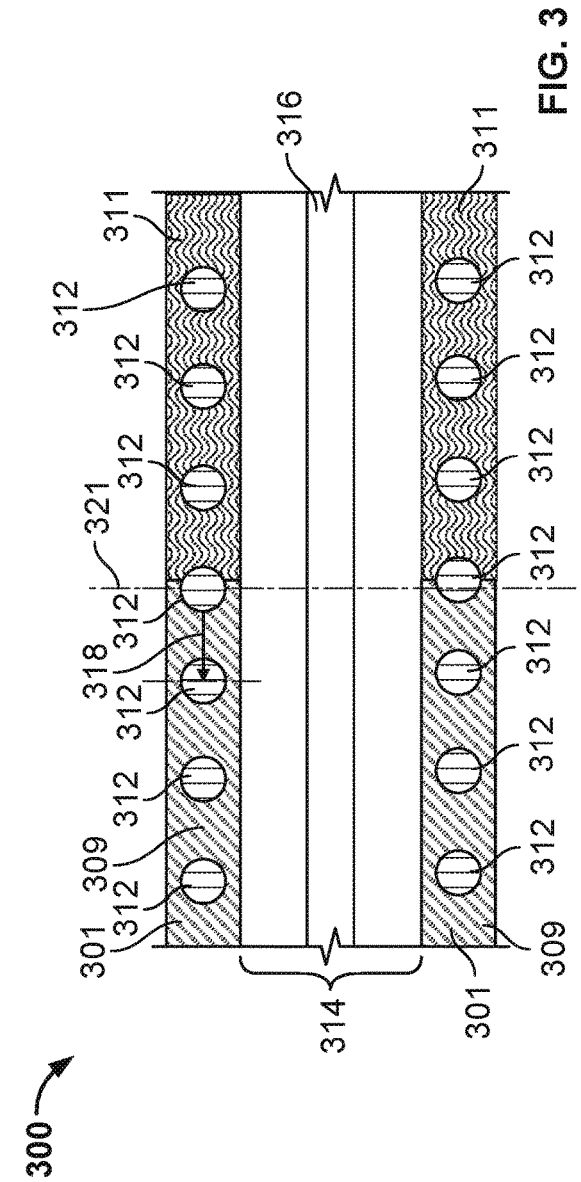

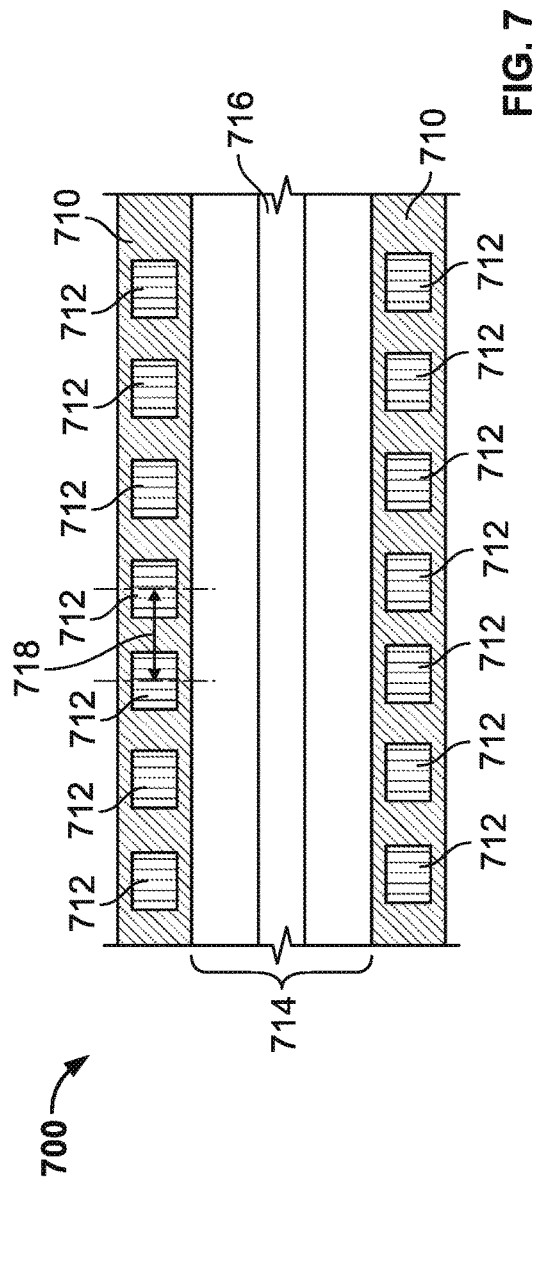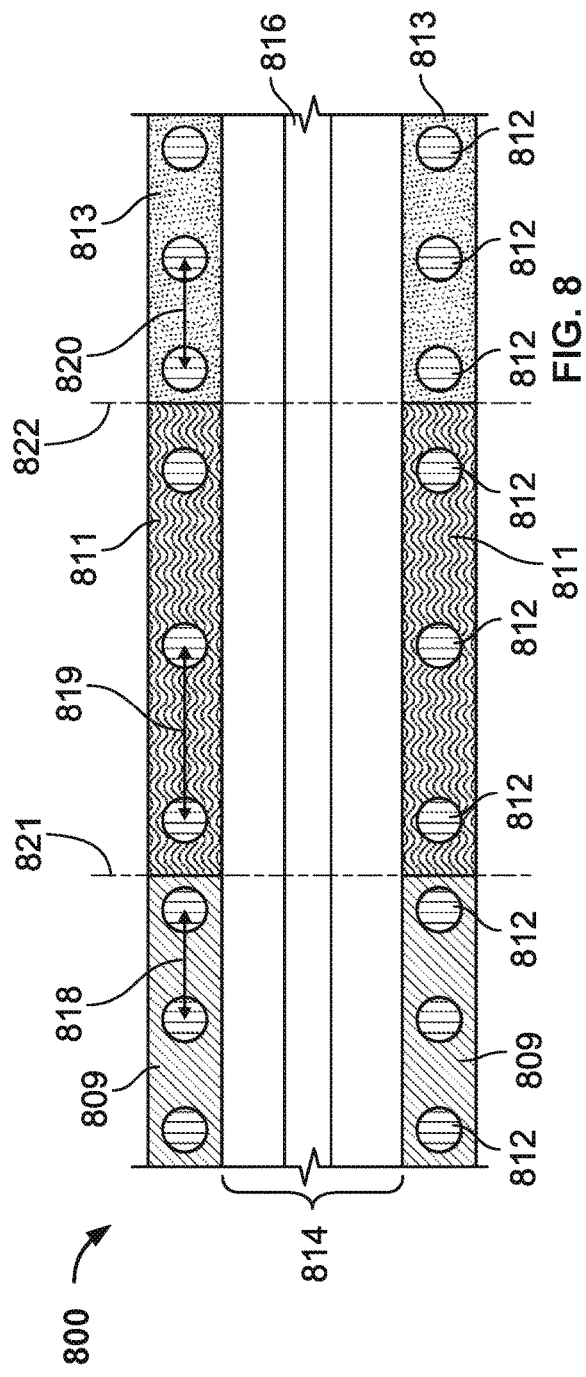

| Cannula Section | Outer Material | Inner Material | Cannula Section Stiffness (Deflexation Force in N. at 15mm) |
|---|---|---|---|
| 1 | TT1065 | TT1065 | 3.0 |
| 2 | TT1055 | TT1065 | 2.6 |
| 3 | TT1055 | TT1055 | 1.6 |
| 4 | TT1055 | Dispensed 55D | 1.8 |
| 5 | TT1065 | Dispensed 55D | 2.8 |
| Conventional | Dispensed 55D | Dispensed 55D | 2.2 |

THERMOFORM CANNULA WITH VARIABLE CANNULA BODY STIFFNESS

CROSS-REFERENCE TO RELATED APPLICATIONS

This application relates to U.S. Pat. No. 6,007,478, for a cannula having constant wall thickness with increasing distal flexibility, the content of which is hereby incorporated herein by reference in its entirety. This application claims priority to U.S. provisional application No. 62/288,914, filed Jan. 29, 2016, the content of which is hereby incorporated herein by reference in its entirety.

BACKGROUND

A blood pump assembly is introduced in the circulatory system to deliver blood between locations in the circulatory system or heart. For example, when the blood pump assembly is deployed in the arterial system the blood pump assembly pulls blood from the left ventricle of the heart and expels the blood into the aorta. In another example, when the blood pump is deployed in the venous system, the blood pump pulls blood from the inferior vena cava, or pulls blood from the right atrium of the heart or the superior vena cava, and expels the blood into the pulmonary artery. Blood pump assemblies are introduced surgically or percutaneously during a cardiac procedure. In one approach when accessing the venous system or right heart, pump assemblies are inserted by a catheterization procedure through the femoral vein using an access sheath (introducer) and a guidewire.

During a catheterization procedure, an introducer is inserted into the femoral vein through an veinotomy to create an insertion path. The insertion path is used to advance a placement guidewire into the artery. For example, the insertion path is used to advance a placement guidewire through the right heart and into the pulmonary artery. Once the guidewire has been inserted into the artery (for example, the pulmonary artery), the pump assembly is backloaded onto the proximal end of the guidewire and pushed into the patient along the guidewire. The pump assembly may include a pump head including an impeller, a cannula, and a catheter.

The pump assembly is commonly loaded by a process called backloading, which involves inserting the proximal end of the guidewire into the distal end of the cannula and then advancing the cannula distally over the guidewire until the pump head is placed in a specified location. Backloading the pump assembly allows the guidewire to remain in position within the patient during the course of a procedure. However, commonly used cannulas of the pump assembly have a tortuous shape, and in some situations the cannula stiffness may prevent the cannula from advancing distally over the guidewire without displacing the guidewire or without extending the length of the procedure. For example, for systems delivering blood from the inferior vena cava to an opening in the pulmonary artery, commonly used cannulas have a fixed stiffness and a 3D shape having two "S" turns. This can make backloading and insertion of the cannula and pump assembly into a patient particularly difficult. The force required to bend a cannula, e.g., during insertion, can be measured as the force in Newtons required to obtain a 15 mm deflection of a cannula sample during a 3-point bend rigidity test.

SUMMARY OF INVENTION

A cannula supporting a percutaneous pump includes a proximal section with a first flexural modulus. The cannula also includes one or more distal sections with a flexural modulus different than the first flexural modulus. The flexural moduli are configured to allow efficient positioning of the cannula in a desired location without displacing the guidewire.

The systems, methods, and devices described herein provide an improved cannula that is configured to facilitate backloading of the pump assembly into the venous system of a patient over a guidewire. The cannula disclosed herein can be inserted into the system of a patient through an arteriotomy, or by veinotomy, or other procedures. The cannula has a stiffness that varies along its length to facilitate backloading of the cannula to a desired location within the heart (e.g., a patient's right heart) without displacing a guidewire. In particular, the cannula is flexible enough at its distal end to follow the guidewire without unnecessary displacement of the guidewire, but stiff enough at its proximal end to guide the cannula into place during backloading. To achieve this variable stiffness, the proximal section of the cannula may be made of a material or combination of materials which is stiffer than a material or combination of materials of the distal section of the guidewire. The lower stiffness of the distal section helps the cannula follow the path of the guidewire, and the higher stiffness of the proximal section increases the force required to buckle the cannula. In addition to facilitating initial delivery, the higher stiffness of the proximal section makes the cannula easier to guide once it has been inserted inside the patient, thereby reducing the amount of force required to exert on the proximal end during insertion. Reducing the amount of force required by varying the stiffness of the proximal section of the cannula also reduces the probability of kinking or buckling of the cannula during insertion. Varying the cannula stiffness also contributes to reducing the delivery time by improving adaptability and conformance to the anatomy of a particular patient, or improving conformance to a wider variation of patient anatomies. The improved cannula is particularly helpful for cannulas having complex or tortuous geometries, such as the cannulas used with the IMPELLA RP® pump or any other pump adapted for use in the right heart (e.g., between the inferior vena cava and the pulmonary artery).

The improved cannula disclosed herein can provide a number of additional advantages. For example, varying the stiffness of the cannula such that different portions of the cannula have different stiffnesses allows the cannula to be better suited for the anatomy of a particular patient, and this better fit helps reduce the delivery time. Furthermore, the variable stiffness cannula can improve manufacturability and can better accommodate larger tolerances for parts or processes.

In one aspect, a system for the insertion of a percutaneous pump comprises a cannula having a proximal inlet, a proximal section, a first distal section, and a distal outlet. The system also comprises a percutaneous pump coupled to the proximal inlet, and a transition zone between the proximal section and the first distal section. The proximal section has a first flexural modulus and the first distal section has a second flexural modulus which is smaller than the first flexural modulus.

In certain implementations, the transition zone is a fused transition zone. In some implementations the fused transition zone may have a length of up to 10 centimeters. Material properties may gradually change over the length of the transition zone.

In certain implementations, the fused transition zone is a thermally fused transition zone.

In certain implementations, the first flexural modulus is configured to increase a buckling force of the cannula and the second flexural modulus is configured to match, (e.g., approximate) or be less than a flexural modulus of a guidewire on which the cannula is backloaded. In some implementations the second flexural modulus may be configured to be significantly less than a flexural modulus of the guidewire on which the cannula is backloaded.

In certain implementations, the distal outlet is configured to be inserted in a ventricle of a heart. In some implementations, the distal outlet is configured to be inserted through the right heart into the pulmonary artery.

In certain implementations, the proximal section of the cannula includes a proximal inner wall made of a first material and a proximal outer wall made of a second material, wherein a flexural modulus of the second material is greater than a flexural modulus of the first material.

In certain implementations, the first flexural modulus is greater than 21,000 psi, and the second flexural modulus is lower than 21,000 psi. In some implementations, the first flexural modulus is between 23,000 psi and 29,000 psi, and the second flexural modulus is between 15,000 psi and 21,000 psi. In some implementations, the first flexural modulus is between 20,000 psi and 35,000 psi, and the second flexural modulus is between 5,000 psi and 15,000 psi.

In certain implementations, the first distal section of the cannula includes a first distal inner wall made of a first material and a first distal outer wall made of a second material, wherein a flexural modulus of the second material is greater than a flexural modulus of the first material.

In certain implementations, the cannula includes an inner wall and an outer wall and a reinforced coil located between the inner wall and an outer wall. In some implementations, the reinforced coil has a constant pitch length.

In certain implementations, a length of the proximal section is between about 10%-50% of a length of the cannula.

In certain implementations, the cannula includes distal sections between the first distal section and a distal end. In some implementations, a second distal section between the first distal section and a distal end. In certain implementations, there is a second fused transition between the first distal section and a second distal section. In some implementations, there is a second thermofused transition between the first distal section and a second distal section.

In certain implementations, a length of the second distal section is between about 10-40% of a length of the cannula.

In certain implementations, a first material of the proximal section is a thermoplastic polyurethane. In some implementations, a first material of the proximal section is a TT1065™ polyurethane. In certain implementations, a second material of the distal section is a thermoplastic polyurethane. In some implementations, a second material of the distal section is a TT1055™ polyurethane.

In another aspect, a cannula is used for inserting a percutaneous pump, the cannula comprising a proximal inlet coupled to the percutaneous pump, a proximal section with a first flexural modulus, and a first distal section thermally fused to the proximal section, the first distal section having a second flexural modulus which is smaller than the first flexural modulus.

In certain implementations, the first flexural modulus is configured to increase a buckling force of the cannula and the second flexural modulus is configured to match a flexural modulus of a guidewire on which the cannula is backloaded.

In certain implementations, the transition zone is a fused transition zone.

In certain implementations, the fused transition zone is a thermally fused transition zone.

In certain implementations, the first flexural modulus is configured to increase a buckling force of the cannula and the second flexural modulus is configured to match, (e.g., approximate) a flexural modulus of a guidewire on which the cannula is backloaded.

In certain implementations, the distal outlet is configured to be inserted in a ventricle of a heart. In some implementations, the distal outlet is configured to be inserted in a right ventricle of the heart.

In certain implementations, the proximal section of the cannula includes a proximal inner wall made of a first material and a proximal outer wall made of a second material, wherein a flexural modulus of the second material is greater than a flexural modulus of the first material.

In certain implementations, the first flexural modulus is greater than 21,000 psi, and the second flexural modulus is lower than 21,000 psi. In some implementations, the first flexural modulus is between 23,000 psi and 29,000 psi, and the second flexural modulus is between 15,000 psi and 21,000 psi. In some implementations, the first flexural modulus is between 20,000 psi and 35,000 psi, and the second flexural modulus is between 5,000 psi and 15,000 psi.

In certain implementations, the first distal section of the cannula includes a first distal inner wall made of a first material and a first distal outer wall made of a second material, wherein a flexural modulus of the second material is greater than a flexural modulus of the first material.

In certain implementations, the cannula includes an inner wall and an outer wall and a reinforced coil located between the inner wall and an outer wall. In some implementations, the reinforced coil has a constant pitch length.

In certain implementations, a length of the proximal section is between about 10%-50% of a length of the cannula.

In certain implementations, the cannula includes distal sections between the first distal section and a distal end. In some implementations, a second distal section between the first distal section and a distal end. In certain implementations, there is a second fused transition between the first distal section and a second distal section. In some implementations, there is a second thermofused transition between the first distal section and a second distal section.

In certain implementations, a length of the second distal section is between about 10-40% of a length of the cannula.

In certain implementations, a first material of the proximal section is a thermoplastic polyurethane. In some implementations, a first material of the proximal section is a TT1065™ polyurethane. In certain implementations, a second material of the distal section is a thermoplastic polyurethane. In some implementations, a second material of the distal section is a TT1055™ polyurethane.

In another aspect, a method for percutaneously inserting a cannula into a ventricle of a heart comprises inserting a distal section of a cannula over a guidewire into the ventricle, and pushing a proximal section of the cannula over the guidewire into the ventricle, where a flexural modulus of the proximal section of the cannula is greater than a flexural modulus of the distal section of the modulus. In some implementations, the ventricle is the right ventricle of the heart.

Variations and modifications will occur to those of skill in the art after reviewing this disclosure. The disclosed features may be implemented, in any combination and subcombination (including multiple dependent combinations and subcombinations), with one or more other features described herein. The various features described or illustrated above, including any components thereof, may be combined or integrated in other systems. Moreover, certain features may be omitted or not implemented.

BRIEF DESCRIPTION OF THE DRAWINGS

The foregoing and other objects and advantages will be apparent upon consideration of the following detailed description, taken in conjunction with the accompanying drawings, in which like reference characters refer to like parts throughout, and in which:

FIG. 2 shows a lateral cross-section of a conventional cannula;

FIG. 3 shows a lateral cross-section of a first illustrative embodiment of a cannula;

FIG. 7 shows a lateral cross-section of a fifth illustrative embodiment of a cannula;

FIG. 8 shows a lateral cross-section of a sixth illustrative embodiment of a cannula;

DETAILED DESCRIPTION

To provide an overall understanding of the systems, methods, and devices described herein, certain illustrative embodiments will be described. Although the embodiments and features described herein are specifically described for use in connection with a percutaneous blood pump system for the right heart, it will be understood that all the components and other features outlined below may be combined with one another in any suitable manner and may be adapted and applied to blood pump systems for the left heart, left ventricle, or other types of cardiac therapy and cardiac assist devices, including balloon pumps, cardiac assist devices implanted using a surgical incision, and the like. Examples of specific implementations and applications are provided primarily for illustrative purposes.

The systems, methods, and devices described herein provide an improved cannula that is configured to facilitate backloading of the cannula into the arterial system of a patient over a guidewire. In particular, the cannula is flexible enough in its distal region to follow the guidewire without unnecessary displacement of the guidewire, but stiff enough at its proximal end to guide the cannula into place during backloading. To achieve this variable stiffness, the proximal section of the cannula may be made of a material or combination of materials which is stiffer than a material or combination of materials of the distal section of the guidewire. The lower stiffness of the distal section helps the cannula follow the path of the guidewire, and the higher stiffness of the proximal section increases the force required to buckle the cannula. In addition to facilitating initial delivery, the higher stiffness of the proximal section makes the cannula easier to guide once it has been inserted inside the patient, thereby reducing the amount of force physicians have to exert on the proximal end during insertion. Reducing the amount of force required also reduces the probability of kinking or buckling of the cannula during insertion. Varying the cannula stiffness also contributes to reducing the delivery time by improving conformance to the anatomy of a particular patient, or improving conformance to a wider range of patient anatomies. The improved cannula is particularly helpful for cannulas having complex or tortuous geometries, such as the cannulas used with the IMPELLA RP® pump or any other pump adapted for use in the right heart (e.g., between the inferior vena cava and the pulmonary artery). Furthermore, the method of manufacturing the improved cannula allows for greater tolerances than manufacturing methods for existing cannulas.

Figure 1:
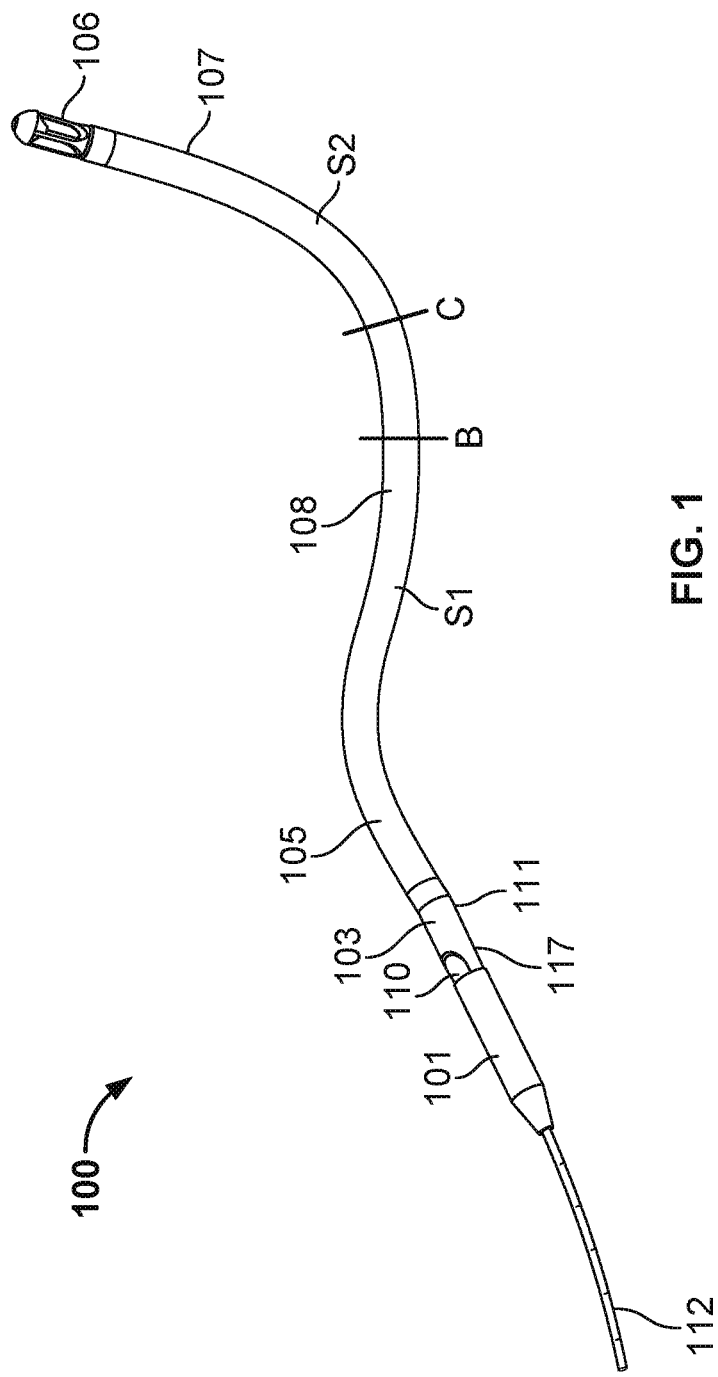
FIG. 1 shows an illustrative embodiment of a cannula assembly.

FIG. 1 shows an illustrative embodiment of a blood pump assembly 100. The skilled artisan will understand that the embodiment of FIG. 1 is illustrative and not intended to limit the scope of the subject matter described herein. The blood pump assembly 100 includes a pump 101, a pump housing 103, a proximal end 105, a distal end 107, a cannula 108, an impeller (not shown), a catheter 112, an inlet area 110, an outlet area 106, and sensor 117. The catheter 112 is connected to the inlet area 110 of the cannula 108. The inlet area 110 is located near the proximal end 105 of the cannula, and the outlet area 106 is located toward the distal end 107 of the cannula 108. The inlet area 110 includes a pump housing 103 with a peripheral wall 111 located radially outward from, and extending about, a rotation axis of the impeller blades (not shown). The impeller (not shown) is rotatably coupled to the pump 101 at the inlet area 110 adjacent to the sensor 117 on the wall 111 of the pump housing 103. The pump housing 103 may be composed of a metal in accordance with implementations.

The embodiments described in FIGS. 2-9 can be applied to a blood pump assembly as shown in FIG. 1, or can be applied to any other blood pump assembly configuration, such as a blood pump assembly including an external motor located at a proximal end of a drive shaft, the external motor controlling blades located at a distal end of the driveshaft.

The cannula 108 has a shape which conforms to the anatomy of the right heart of a patient. In this exemplary embodiment, the cannula has a proximal end 105 arranged to be located near the patient's inferior vena cava, and a distal end 107 arranged to be located near the pulmonary artery. The cannula 108 includes a first segment S1 extending from the inflow area to a point B between the inlet area 110 and the outlet area 106. The cannula 108 also includes a second segment S2 extending from a point C, which is an inflection between the inlet area 110 and the outlet area 106, to the outlet area 106. In some implementations, B and C may be at the same location along the cannula 108. The first segment S1 of the cannula is curved, for example forming an 'S' shape in a first plane. In some implementations, the segment S1 can have curvatures between about 30° and 180° (e.g., 40°, 50°, 60°, 70°, 80°, 90°, 100°, 110°, 120°, 130°, 140°, 150°, 160°, or 170°). The second segment S2 of the cannula is curved, for example forming an 'S' shape in a second plane. In some implementations, segment S2 can have curvatures between about 30° and 180° (e.g., 40°, 50°, 60°, 70°, 80°, 90°, 100°, 110°, 120°, 130°, 1400, 1500, 160°, or 170°). The second plane can be different from the first plane. In some implementations, the second plane is parallel or identical to the first plane. In certain implementations, the second plane is oblique or perpendicular to the first plane.

FIG. 2 shows a lateral cross-section of a conventional cannula 200 labeled as prior art. The skilled artisan will understand that the embodiment of FIG. 2 is illustrative and not intended to limit the scope of the subject matter described herein. The conventional cannula includes a main section 210, a coil wire 212, and a bore through which the blood circulates, referred to as the lumen 214, through which passes a guidewire 216. The coil wire 212 is located within a wall of the main section 210. The coil wire 212 comprises a wire of circular cross section, such as a round wire. In the embodiment of FIG. 2, and in any other embodiment described herein in FIGS. 2-9, the coil wire 212 or its equivalent is positioned over a first inner layer, and covered and sealed by a second layer, e.g. a lamination layer. The materials of the first inner layer and second outer layer, located respectively below and above the coil wire 212 may be different materials or may be made of the same material. For example, the coil wire 212 is located between an inner layer (e.g., a thermoplastic polyurethane such as Dermopan) and an outer layer (e.g., a thermoplastic polyurethane such as TT1065). The main section 210 is made of a single material, for example dispensed 55D polyurethane. The main section 210 has a constant outer diameter and a constant inner diameter, and the coil wire 212 has a constant pitch 218, made of the single material. As a result, the main section 210 has a constant flexural modulus.

As discussed above, when a cannula (e.g., cannula 200 in FIG. 2) is too stiff, backloading and insertion of a pump assembly (e.g., pump assembly 100 in FIG. 1) into a patient may be undesirably difficult. Accordingly, some physicians may use a cannula with a coil wire which has a variable pitch length to modify the stiffness of the cannula and to position the cannula without displacing the guidewire 216 out of the pulmonary valve. However, when the coil wire pitch length is varied, the kink resistance of the cannula may be compromised because the coil wire pitch length affects the minimum bend radius of the cannula. Furthermore, for particular pumps, such as the IMPELLA RP® pump which is used in combination with a curved cannula (e.g., cannula 108 in FIG. 1), decreasing kink resistance by varying the coil wire pitch length may result in damage to the patient's artery because varying the coil wire pitch length affects the spring constant of the cannula and makes the cannula harder to control.

FIG. 3 shows a lateral cross-section of a first illustrative embodiment of a cannula 300, having a similar general structure as the cannula 108 (FIG. 1) but including a variable stiffness along its length. The skilled artisan will understand that the embodiment of FIG. 3 is illustrative and not intended to limit the scope of the subject matter described herein. The cannula 300 has a variable stiffness along its length. The stiffness of the cannula 300 may vary along its length due to the use of different materials, the use of a variable diameter or coil pitch, and/or a combination of the use of different materials and a variable diameter or coil pitch. The cannula 300 includes a proximal section 309, which is near the impeller, a first distal section 311, which is near the pump head, a transition region 321, a coil wire 312 wound around the cannula, a lumen 314, and a guidewire 316. The guidewire 316 passes through the lumen 314. Instead of a single main section 210 as in the conventional cannula 200, the cannula 300 includes two sections, the proximal section 309 and the first distal section 311. The proximal section 309 is used to push the cannula onto the guidewire 316. The first distal section 311 follows the guidewire 316 to enter the patient and is coupled to the proximal section 309 by the transition region 321. In some embodiments, the transition region spans between 10-20% of the cannula length and has a flexibility modulus that varies from its proximal to distal ends, thereby joining the proximal and distal regions of the cannula with a variable flexural modulus. The coil wire 312 is located within a wall 301 of the proximal section 309 and the first distal section 311.

The proximal section 309 is made of a first material. The first material may have a flexural modulus between about 20,000 psi and 30,000 psi, preferably between 23,000 psi and 29,000 psi. The first material may have a first flexural modulus between 20,000 psi and 35,000 psi. For example, the proximal section 309 may be made of TT1065™ TPU (thermoplastic polyurethane), a thermoplastic, a polymer, or any other material that becomes pliable above a specific temperature and solidifies upon cooling. For example, the proximal section 309 may be constructed of preferred thermoplastics (e.g., polyurethanes) exhibiting solvent resistance and biostability over a wide range of hardnesses and can be configured to have varied hardness levels. The proximal section 309 has a constant diameter, the coil wire 312 has a constant pitch 318, and the proximal section 309 has a first flexural modulus.

The first distal section 311 is made of a second material, for example a material with a flexural modulus between about 10,000 psi and 22,000 psi, preferably between 15,000 psi and 21,000 psi. The second material may have a second flexural modulus between 5,000 psi and 15,000 psi. For example, the first distal section 311 may be made of TT1055™ TPU. The first distal section 311 has a constant diameter, the coil wire 312 has a constant pitch 318, and the first distal section 311 has a second flexural modulus. The second flexural modulus is smaller than the first flexural modulus of the proximal section 309. In some implementations, no coil wire is included in the cannula 300 (and thereby reducing the tendency of the cannula to buckle).

The lower stiffness of the first distal section 311 helps the cannula 300 follow the path of the guidewire 316. Simultaneously, the higher stiffness of the proximal section 309 improves delivery of the cannula 300 by increasing the buckling force of the cannula 300. The higher stiffness of the proximal section 309 also makes it easier to convert force applied on the cannula 300 into movement of the cannula inside the patient, thereby reducing the amount of force required to exert on the proximal end during insertion. The higher stiffness of the proximal section also reduces the probability that the cannula 300 will kink or buckle during insertion.

Figure 4:
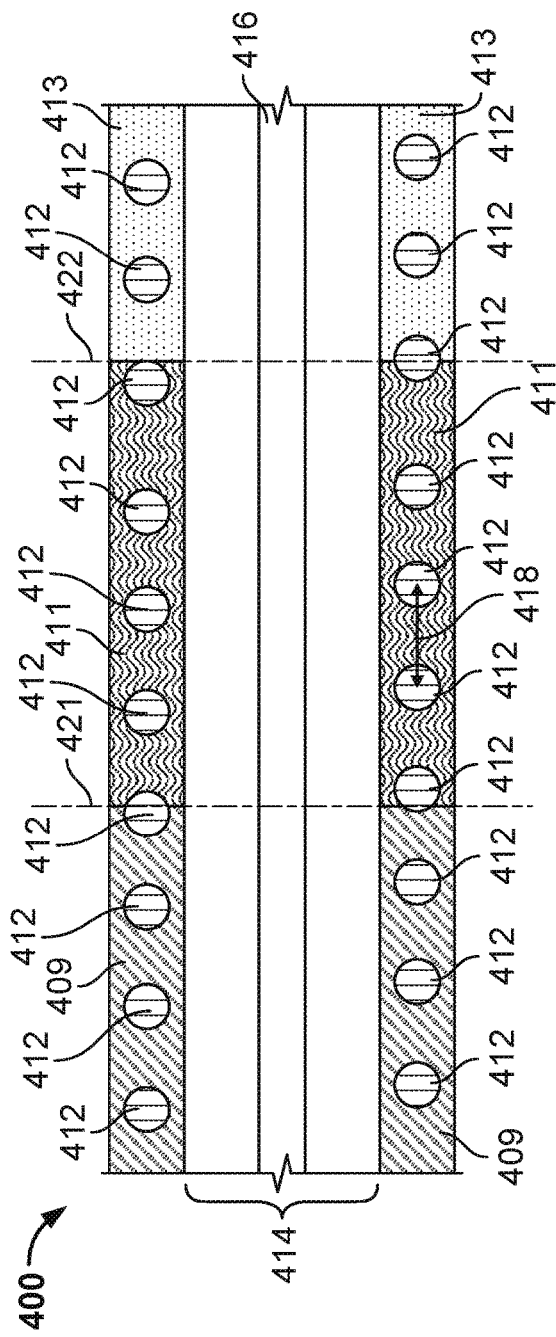
FIG. 4 shows a lateral cross-section of a second illustrative embodiment of a cannula.

To further reduce the probability of kinking or buckling during insertion, the stiffness of the cannula can be varied along its length, for example over three different sections, as shown in FIG. 4. FIG. 4 shows a lateral cross-section of a second illustrative embodiment of a cannula 400. The skilled artisan will understand that the embodiment of FIG. 4 is illustrative and not intended to limit the scope of the subject matter described herein. The cannula 400 has a variable stiffness along its length. The stiffness of the cannula 400 may vary along its length due to the use of different materials, the use of a variable diameter or coil pitch, and/or a combination of the use of different materials and a variable diameter or coil pitch. The cannula 400 includes a proximal section 409, a first transition region 421, a first distal section 411, a second transition region 422, a second distal section 413, a coil wire 412 wound around the cannula, a lumen 414, and a guidewire 416. The guidewire 416 passes through the lumen 414.

Instead of a single main section 210 as in the conventional cannula 200, the cannula 400 of FIG. 4 includes three sections, the proximal section 409, the first distal section 411 and the second distal section 413. As shown, the first distal section is fit between the proximal section and the second distal section. The stiffness in the proximal, first distal and second distal sections will preferably vary. The proximal section 409 can be used by physicians to push the cannula onto the guidewire 416, the first distal section 411 retains its shape but follows the guidewire inside the patient, and the second distal section 413 follows the guidewire 416 to enter the patient. The proximal section 409 and the first distal section 411 are coupled by the first transition region 421, which may be a thermofused transition region, a heat shrink sleeve or a lap joint. The first distal section 411 and the second distal section 413 are coupled by the second transition region 422, which may be a thermofused transition. As referred to herein "thermofused" means connected as a result of a thermic reaction between materials. For example, a first distal section 411 made of plastic may be thermofused with a second distal section 413 made of plastic. A transition refers to the region connecting two elements, such as the region where a plastic of the first distal section fused with a plastic of the second distal section by a thermic reaction.

In the embodiment shown in FIG. 4, the coil wire 412 is located within the wall of the proximal section 409, the first distal section 411, and the second distal section 413. In some implementations, no coil wire is included. The proximal section 409 can be made of a first material. For example, the first material may be TT1065™ polyurethane. The proximal section 409 may have a constant diameter, the coil wire 412 may have a constant pitch 418, and the proximal section 409 may have a first flexural modulus. The first distal section 411 is made of a second material. For example, the second material may be TT1055™ polyurethane. The first distal section 411 has a constant diameter, the coil wire 412 has a constant pitch 418, and the first distal section 411 has a second flexural modulus. The second flexural modulus is smaller than the first flexural modulus of the proximal section 409. The second distal section 413 is made of a third material. For example, the third material may be TT1055™ polyurethane. The second distal section 413 has a constant diameter, the coil wire 412 has a constant pitch 418, and the second distal section 413 has a third flexural modulus. The third flexural modulus is smaller than the first flexural modulus of the proximal section 409 and the second flexural modulus of the first distal section 411. In some implementations transitions 421 and 422 may be any other type of transition, such as transition using adhesives or fasteners, a transition created by interference fits, or as a result of welding or overmolding.

Alternatively, at any transition described in FIGS. 2-9, for example transition region 422 between the first distal section 411 and the second distal section 413 in FIG. 4, two sections may be connected by using a solvent material or an adhesive material. Alternatively, a heat shrink sleeve may be positioned over the transition region to seal both sections together. A lap joint may be used to connect both sections. A transition region may use a vertical transition such as transition region 422 as shown in FIG. 4, or a transition with a tapered or angled cross-section, to reduce the potential for kinks to develop at the transition region.

In the embodiment of FIG. 4, the presence of three sections instead of two sections further improves the cannula with respect to the embodiment in FIG. 2. For example, three sections may be used to conform to the anatomy of a particular patient, or to conform to different types of patient anatomies. As noted above, varying the cannula stiffness can facilitate delivery. The lower stiffness of the second distal section 413 helps the cannula 400 follow the path of the guidewire 416. The stiffness of the first distal section 411 enables the first distal section to also follow the path of the guidewire and simultaneously to better transmit force applied on the proximal section 409. As noted above, the higher stiffness of the proximal section 409 improves delivery of the cannula 400.

Figure 5:
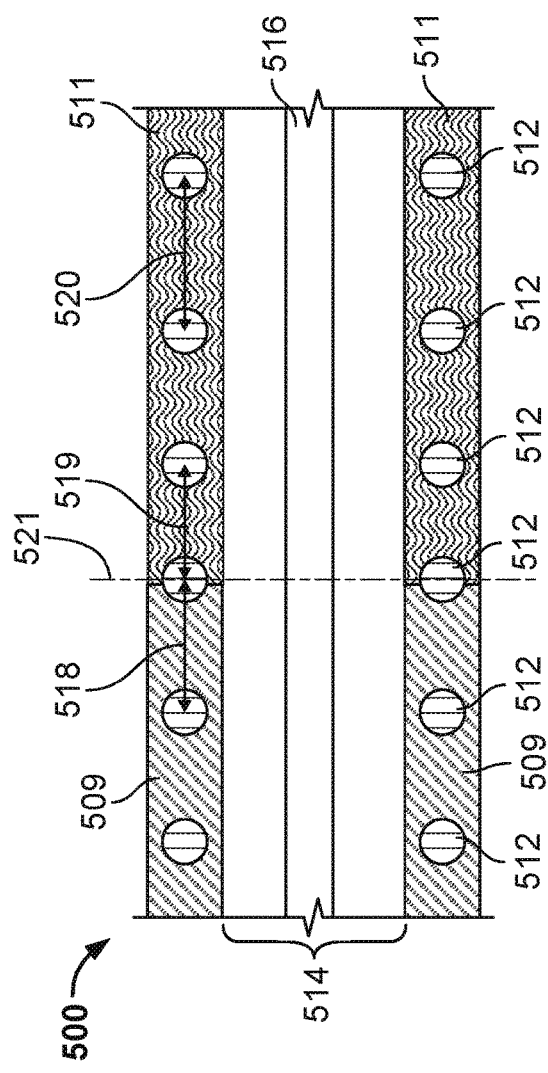
FIG. 5 shows a lateral cross-section of a third illustrative embodiment of a cannula.

FIG. 5 shows a lateral cross-section of a third illustrative embodiment of a cannula 500 having a cannula with multiple sections that provide varying stiffness along the length of the cannula. The skilled artisan will understand that the embodiment of FIG. 5 is illustrative and not intended to limit the scope of the subject matter described herein. The cannula 500 has a variable stiffness along its length. The stiffness of the cannula 500 may vary along its length due to the use of different materials, the use of a variable diameter or coil pitch, and/or a combination of the use of different materials and a variable diameter or coil pitch. The cannula 500 includes a proximal section 509, a transition 521, a first distal section 511, a coil wire 512, a lumen 514, and a guidewire 516. The guidewire 516 passes through the lumen 514. Instead of a single main section 210 as in the conventional cannula 200, the cannula 500 includes two sections, the proximal section 509 and the first distal section 511. The proximal section 509 can be used by physicians to push the cannula onto the guidewire 516. The first distal section 511 follows the guidewire 516 to enter the patient, and is coupled to the proximal section 509 by the transition 521. The coil wire 512 is located within the wall of the proximal section and the first distal section. The proximal section 509 is made of a first material. For example, the first material may be TT1065™ polyurethane. The first distal section 511 is made of a second material. For example, the second material may be TT1055™ polyurethane. The proximal section 509 and the first distal section 511 have constant diameters. The coil wire 512 has a variable pitch which increases along a longitudinal axis of the cannula, with coil wire pitch 518 being smaller than coil wire pitch 519 and greater than coil wire pitch 520, the smaller pitch resulting in higher rigidity. In some implementations, the coil wire pitch may be constant for proximal section 509, and the coil wire pitch may be constant for first distal section 511 but smaller than the coil wire pitch for proximal section 509. The proximal section 509 has a first flexural modulus, and the first distal section 511 has a second flexural modulus. The second flexural modulus is smaller than the first flexural modulus of the proximal section 509. The stiffness of the cannula (and its deliverability) are improved by using a coil wire 512 with a decreasing pitch, and by selecting materials with differing flexural moduli for the proximal section 509 and the first distal section 511. The combination of these features varies the cannula's stiffness, thereby facilitating delivery.

Figure 6:
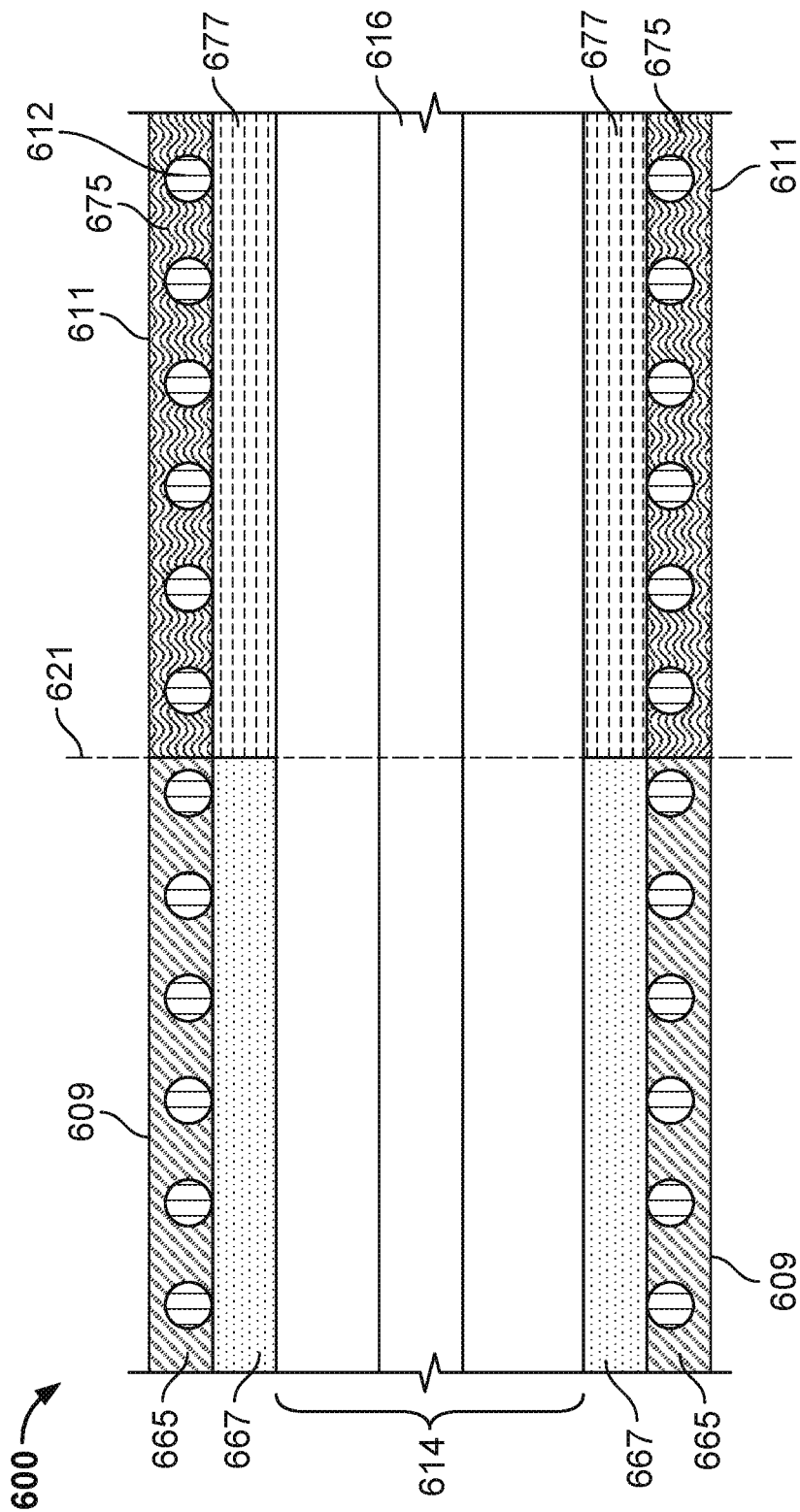
FIG. 6 shows a lateral cross-section of a fourth illustrative embodiment of a cannula.

FIG. 6 shows a lateral cross-section of a fourth illustrative embodiment of a cannula 600. The skilled artisan will understand that the embodiment of FIG. 6 is illustrative and not intended to limit the scope of the subject matter described herein. The cannula 600 has a variable stiffness along its length. The stiffness of the cannula 600 may vary along its length due to the use of different materials, the use of a variable diameter or coil pitch, and/or a combination of the use of different materials and a variable diameter or coil pitch. The cannula 600 includes a proximal section 609, a first distal section 611, a coil wire 612, a lumen 614, and a guidewire 616. The cannula may include a coil wire 612, similar to the coil wires described in relation to FIGS. 2-5 and FIGS. 7-9 that follow. The guidewire 616 passes through the lumen 614. Instead of using a uniform material for the proximal section wall and using a uniform material for the first distal section wall, as in the conventional cannula 200, for each section the cannula 500 includes an inner layer and an outer layer which are concentric and use different materials, a first material in the inner layer and a second material in the outer layer. The proximal section 609 is made of an inner layer 667 and an outer layer 665. The first distal section 611 is made of an inner layer 677 and an outer layer 675. The proximal section 609 has a first flexural modulus, and the first distal section 611 has a second flexural modulus. The second flexural modulus is smaller than the first flexural modulus of the proximal section 609. The presence of an inner layer 667 and an outer layer 675 with different material properties, in combination with a proximal section 609 and the first distal section 611 having different flexural moduli further improves delivery of the cannula. The stiffness of the cannula can be modified by selecting material properties both in a longitudinal (proximal-distal) direction and in a radial (inner-outer) direction. For example, the flexural modulus for the first section is greater than 10,000 psi, and the flexural modulus for the second section is smaller than 10,000 psi. In another example, the flexural modulus for the first section is equal to or greater than 23,000 psi, and the flexural modulus for the second section is equal to or lower than 15,000 psi. As noted above, varying the cannula stiffness can reduce the delivery time.

FIG. 7 shows a lateral cross-section of a fifth illustrative embodiment of a cannula 700. The skilled artisan will understand that the embodiment of FIG. 7 is illustrative and not intended to limit the scope of the subject matter described herein. The cannula 700 includes a main section 710, a coil wire 712, and a bore through which the blood circulates, referred to as the lumen 714, through which passes a guidewire 716. The coil wire 712 is located within a wall of the main section 710. In this fifth embodiment, the coil wire 712 comprises a wire of rectangular cross section, such as a wire ribbon. In the embodiment of FIG. 7, and in any other embodiment described herein in FIGS. 2-6 and 8-9, the coil wire 712 or its equivalent is positioned over a first inner layer, and covered and sealed by a second layer, e.g. a lamination layer. The materials of the first inner layer and second outer layer, located respectively below and above the coil wire 712 may be different materials or may be made of the same material. For example, the coil wire 712 is located between an inner layer (e.g., a thermoplastic polyurethane such as Dermopan) and an outer layer (e.g., a thermoplastic polyurethane such as TT1065). The main section 710 is made of a single material, for example dispensed 55D polyurethane. The main section 710 has a constant outer diameter and a constant inner diameter, and the coil wire 712 has a constant pitch 718, made of the single material. As a result, the main section 710 has a constant flexural modulus.

FIG. 8 shows a lateral cross-section of a sixth illustrative embodiment of a cannula 800 having a cannula with multiple sections that provide varying stiffness along the length of the cannula. The skilled artisan will understand that the embodiment of FIG. 8 is illustrative and not intended to limit the scope of the subject matter described herein. The cannula 800 has a variable stiffness along its length. The stiffness of the cannula 800 may vary along its length due to the use of different materials, the use of a variable diameter or coil pitch, and/or a combination of the use of different materials and a variable diameter or coil pitch. The cannula 800 includes a proximal section 809, a first transition 821, a first distal section 811, a second transition 822, a second distal section 813, a coil wire 812, a lumen 814, and a guidewire 816. The guidewire 816 passes through the lumen 814. Instead of a single main section 810 as in the conventional cannula 200 shown in FIG. 2, the cannula 800 includes three sections, the proximal section 809, the first distal section 811, and the second distal section 813. The proximal section 809 can be used by physicians to push the cannula onto the guidewire 816. The first distal section 811 and the second distal section 813 follows the guidewire 816 to enter the patient, where the first distal section 811 is coupled to the proximal section 809 by the first transition 821. The coil wire 812 is located within the wall of the proximal section 809, the first distal section 811 and the second distal section 813. The coil wire 812 may comprise a round wire. The proximal section 809 is made of a first material. For example, the first material may be TT1065™ polyurethane. The first distal section 811 is made of a second material. For example, the second material may be TT1055™ polyurethane. The second distal section 813 is made of a third material. For example, the third material may be TT1065™ polyurethane. The proximal section 809, the first distal section 811 and the second distal section 813 have constant diameters. The coil wire 812 has a variable pitch which increases along a longitudinal axis of the cannula, with coil wire pitch 818 being smaller than coil wire pitch 819 and greater than coil wire pitch 820, the smaller pitch resulting in higher rigidity. In some implementations, the coil wire pitch may be constant for proximal section 809, and the coil wire pitch may be constant for first distal section 811 but smaller than the coil wire pitch for proximal section 809, and, further, the coil wire pitch may be constant for second distal section 813 but smaller than the coil wire pitch for proximal section 809. The proximal section 509 has a first flexural modulus, the first distal section 811 has a second flexural modulus, and the second distal section 813 has a third flexural modulus. The second flexural modulus and the third flexural modulus are each smaller than the first flexural modulus of the proximal section 809. The stiffness of the cannula (and its deliverability) are improved by using a coil wire 812 with a decreasing pitch, and by selecting materials with differing flexural moduli for the proximal section 809 and the first distal section 811. The combination of these features varies the cannula's stiffness, thereby facilitating delivery. In certain embodiments, the coil wire 812 may comprise a wire ribbon. In certain embodiments, the coil wire pitches 818-820 may differ from each other, and in other embodiments, at least two of the pitches 818-820 may be the same.

Figure 9:
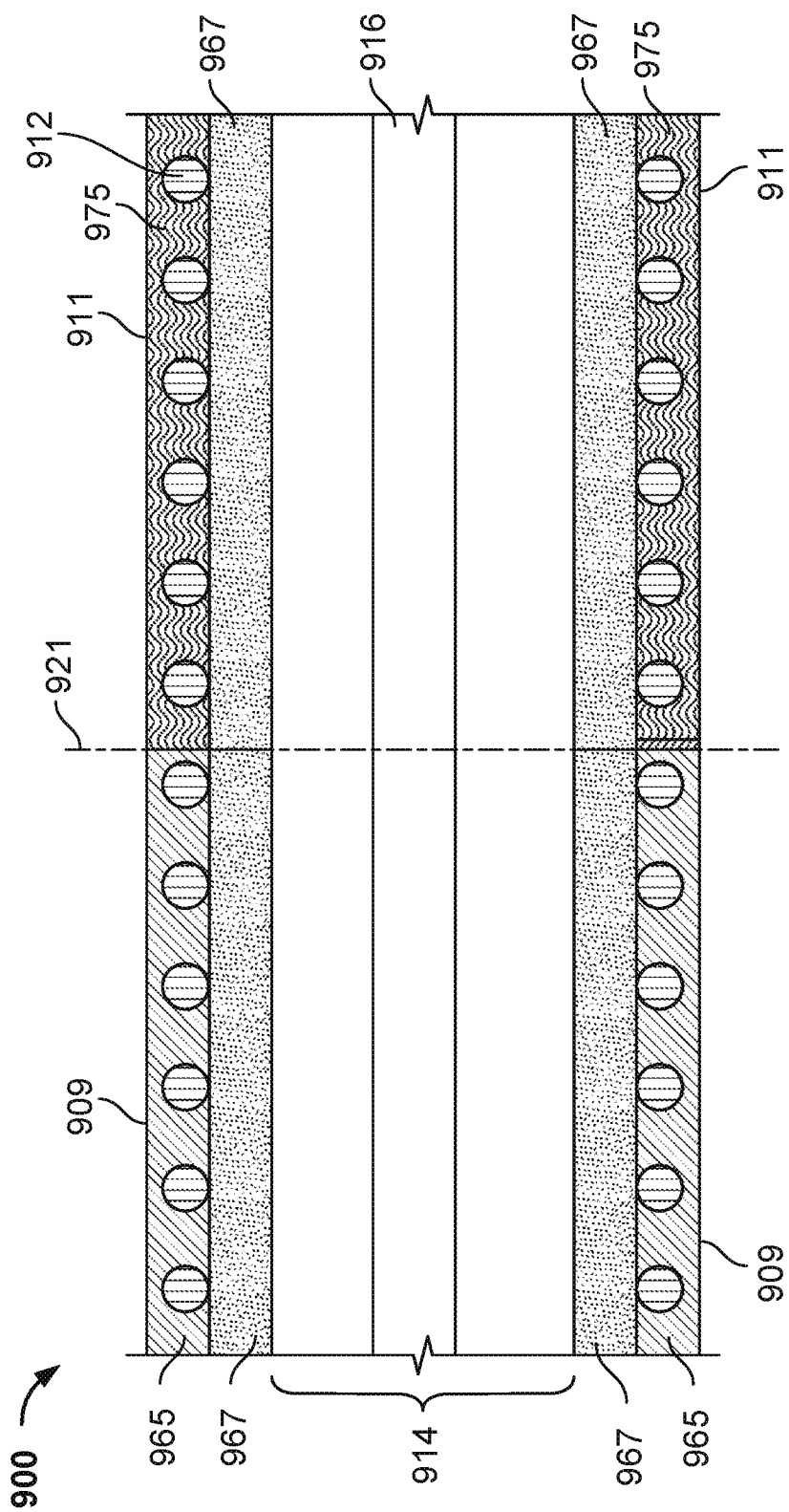
FIG. 9 shows a lateral cross-section of a seventh illustrative embodiment of a cannula.

FIG. 9 shows a lateral cross-section of a seventh illustrative embodiment of a cannula 900. The skilled artisan will understand that the embodiment of FIG. 9 is illustrative and not intended to limit the scope of the subject matter described herein. The cannula 900 has a variable stiffness along its length. The stiffness of the cannula 900 may vary along its length due to the use of different materials, the use of a variable diameter or coil pitch, and/or a combination of the use of different materials and a variable diameter or coil pitch. The cannula 900 includes a proximal section 909, a first distal section 911, a coil wire 912, a lumen 914, and a guidewire 916. The cannula may include a coil wire 912, similar to the coil wires described in relation to FIGS. 2-8, that is the coil wire 812 may comprise a round wire or a wire ribbon. The guidewire 916 passes through the lumen 914.

Instead of using a uniform material for the proximal section wall and using a uniform material for the first distal section wall, as in the conventional cannula 200, for each section the cannula 900 includes an inner layer and an outer layer which are concentric and use different materials, a first material in the inner layer and a second material in the outer layer. The proximal section 909 is made of an inner layer 967 and an outer layer 965. The first distal section 911 is made of the same inner layer 967 and an outer layer 975. Therefore in this embodiment, the inner layer 967 lines the inner surface of the proximal section 909 and the first distal section 911. As the inner layer 967 of cannula 900 is the same for both the proximal section 909 and first distal section 911, cannula 900 offers improved manufacturability. The proximal section 909 has a first flexural modulus, and the first distal section 911 has a second flexural modulus. The second flexural modulus is smaller than the first flexural modulus of the proximal section 909. The presence of an inner layer 967 and an outer layer 975 with different material properties, in combination with a proximal section 909 and the first distal section 911 having different flexural moduli further improves delivery of the cannula. The stiffness of the cannula can be modified by selecting material properties both in a longitudinal (proximal-distal) direction and in a radial (inner-outer) direction. For example, the flexural modulus for the first section is greater than 10,000 psi, and the flexural modulus for the second section is smaller than 10,000 psi. In another example, the flexural modulus for the first section is equal to or greater than 23,000 psi, and the flexural modulus for the second section is equal to or lower than 15,000 psi. As noted above, varying the cannula stiffness can reduce the delivery time.

Figures 10, 11:
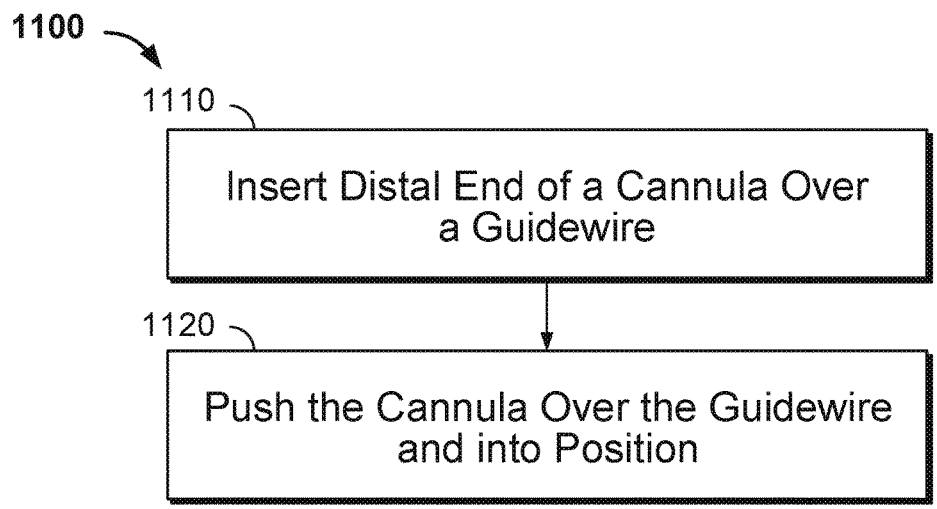
FIG. 10 shows a table of data related to properties of the cannula in FIGS. 2-9.
FIG. 11 shows an illustrative process for inserting a cannula.

FIG. 10 shows a table summarizing material properties of exemplary embodiments of the cannula shown in FIGS. 2-9. The skilled artisan will understand that the table of FIG. 10 is illustrative and not intended to limit the scope of the subject matter described herein. The table indicates combinations of materials used for an inner layer of a cannula, for example layer 667 in FIG. 6 and materials used for an outer layer of a cannula, for example layer 665 in FIG. 6, along with the resulting cannula section stiffness, for example the stiffness of the proximal section 609 in FIG. 6, measured as the force in Newtons required to obtain a 15 mm deflection during a 3-point bend rigidity test for a cannula sample with a constant coil pitch length. As indicated in FIG. 10, certain combinations of inner and outer materials require less force to obtain the 15 mm deflection than the conventional cannula section. For example, only 1.6 N are required for a TT1055™ inner layer and a TT1055™ outer layer as opposed to the 2.2 N required for a conventional cannula with inner and outer layers made of the same Dispensed 55D material. The flexural modulus for TT1055™ may be lower than 21,000 psi, e.g., between 15,000 psi and 21,000 psi, and the flexural modulus for TT1065™ may be greater than 21,000 psi, e.g., between 23,000 psi and 29,000 psi. The flexural modulus for the second material (e.g., TT1055™) may be 18,000 psi and the flexural modulus for the first material (e.g., TT1065™) may be 26,000 psi.

FIG. 11 shows a method 1100 for inserting a cannula according to certain implementations. The skilled artisan will understand that the method of FIG. 11 is illustrative and not intended to limit the scope of the subject matter described herein. The method 1100 may be implemented to insert a cannula which is part of a pump assembly (e.g., pump assembly 100 shown in FIG. 1) onto a guidewire using a cannula, as disclosed or enabled by this disclosure, for example the cannulas described in any of the aforementioned implementations in FIGS. 2-9. The cannulas in the aforementioned implementations of FIGS. 2-9 have a variable stiffness along its length. The stiffness of the cannulas may vary along their lengths due to the use of different materials, due to the use of a variable diameter or coil pitch, and/or due to a combination of the use of different materials and a variable diameter or coil pitch. The cannula may have a shape which matches the anatomy of a heart. For example, the cannula may have a shape which matches the right heart, e.g., the shape of the right ventricle.

In step 1110, the distal end of the cannula is inserted over a guidewire. The cannula includes a proximal section and a distal section which can include more than one distal section, such as first and second distal sections or more. The proximal section may be used to push the cannula onto the guidewire. The distal sections follow the guidewire to enter the patient and are coupled to the proximal section. The proximal section may be stiffer than the distal sections. A lower stiffness of a distal section helps the cannula follow the path of the guidewire. Simultaneously, the higher stiffness of the proximal section improves delivery of the cannula by increasing the buckling force of the cannula. The higher stiffness of the proximal section also makes easier transmitting force applied on the cannula into movement of the cannula inside the patient, thereby reducing the amount of force physicians have to exert on the proximal end during insertion. The variable stiffness of the cannula can reduce the delivery time from an average delivery time of between about 5 minutes and 15 minutes (depending on the patient and procedure) to an average of about 2 minutes to 5 minutes or less.

The method 1100 further includes positioning a distal section of the cannula over the guidewire and applying pressure on the proximal section of the cannula to position the cannula in a desired location without displacing the guidewire (step 1120). The proximal section may be used to push the cannula to its desired location. The proximal section may be stiffer than the distal section. The higher stiffness of the proximal section also makes easier transmitting force applied on the cannula into movement of the cannula inside the patient, thereby reducing the amount of force required to exert on the proximal end during insertion. Simultaneously, a lower stiffness of the distal section (e.g., first distal section) offers a lower resistance as the cannula is pushed along the path of the guidewire. The variable stiffness of the cannula can reduce the delivery time from an average delivery time of between about 5 minutes and 15 minutes (depending on the patient and procedure) to an average of about 2 minutes to 5 minutes or less.

Variations and modifications will occur to those of skill in the art after reviewing this disclosure. For example, in some implementations, any of the alternative embodiments described in FIGS. 2-11 may be combined. For example, the varying pitch coil structure of the cannula in FIG. 5 may be combined with the different guidewire materials described with respect to FIGS. 2-10. In another example, the different inner and outer layers of FIG. 6 may be combined with any of the proximal and distal material combinations shown in FIGS. 2-5 and 7-9. The disclosed features may be implemented, in any combination and subcombination (including multiple dependent combinations and subcombinations), with one or more other features described herein. Further, while the cannula described in the aforementioned sections comprises various grades of polyurethane, it will be understood that other material choices are available. These include high-density polyethylene (HDPE) material, medium-density polyethylene (MDPE) material, low-density polyethylene (LDPE) material, polyether ether ketone (PEEK), polyether block amide (such as PEBAX) and polyester. The various features described or illustrated above, including any components thereof, may be combined or integrated in other systems. Moreover, certain features may be omitted or not implemented. For example, the internal structure of the cannulas described in the aforementioned embodiments may be adopted in a corkscrew shape cannula which could be made using a thermoform process, such as that described in U.S. patent application Ser. No. 15/156,570, the content of which is hereby incorporated herein by reference in its entirety.

It is important to note that the constructions and arrangements of apparatuses or the components thereof as shown in the various exemplary implementations are illustrative only. Although only a few implementations have been described in detail in this disclosure, those skilled in the art who review this disclosure will readily appreciate that many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter disclosed. For example, elements shown as integrally formed may be constructed of multiple parts or elements, the position of elements may be reversed or otherwise varied, and the nature or number of discrete elements or positions may be altered or varied. The order or sequence of any process or method steps may be varied or re-sequenced according to alternative implementations. Other substitutions, modifications, changes and omissions may also be made in the design, operating conditions and arrangement of the various exemplary implementations without departing from the scope of the present disclosure.

While various inventive implementations have been described and illustrated herein, those of ordinary skill in the art will readily envision a variety of other mechanisms and/or structures for performing the function and/or obtaining the results and/or one or more of the advantages described herein, and each of such variations and/or modifications is deemed to be within the scope of the inventive implementations described herein. More generally, those skilled in the art will readily appreciate that, unless otherwise noted, any parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive implementations described herein. It is, therefore, to be understood that the foregoing implementations are presented by way of example only and that, within the scope of the appended claims and equivalents thereto, inventive implementations may be practiced otherwise than as specifically described and claimed. Inventive implementations of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

For the purpose of this disclosure, the termed "coupled" means the joining of two members directly or indirectly to one another. Such joining may be stationary or moveable in nature. Such joining may be achieved with the two members or the two members and any additional intermediate members being integrally formed as a single unitary body with one another or within the two members of the two members and any additional intermediate members being attached to one another. Such joining may be permanent in nature or may be removable or releasable in nature.

The indefinite articles "a" and "an," as used herein in the specification and in the claims, unless clearly indicated to the contrary, should be understood to mean "at least one." As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of" will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of."

In the claims, as well as in the specification above, all transitional phrases such as "comprising," "including," "carrying," "having," "containing," "involving," "holding," "composed of," and the like are to be understood to be open-ended, i.e., to mean including but not limited to.

The claims should not be read as limited to the described order or elements unless stated to that effect. It should be understood that various changes in form and detail may be made by one of ordinary skill in the art without departing from the spirit and scope of the appended claims. All implementations that come within the spirit and scope of the following claims and equivalents thereto are claimed.

Examples of changes, substitutions, and alterations are ascertainable by one skilled in the art and could be made without departing from the scope of the information disclosed herein. All references cited herein are incorporated by reference in their entirety and made part of this application.

We claim:

1. A percutaneous pump system, the system comprising:
   a cannula having a proximal opening, a proximal section, a first distal section, a distal opening, and a bore extending between the distal and proximal openings;
   a percutaneous pump comprising an impeller and coupled to the cannula and configured to circulate blood through the bore of the cannula when the percutaneous pump is disposed in a vasculature of a patient; and
   the cannula having a transition zone between the proximal section and the first distal section,
   wherein the proximal section has a first flexural modulus that is constant along its length, and the first distal section has a second flexural modulus that is constant along its length and which is smaller than the first flexural modulus, and
   wherein the proximal section forms a first curve in a first plane, the first distal section forms a second curve in a second plane different from the first plane, and
   wherein the proximal section of the cannula includes a proximal inner wall made of a first material and a proximal outer wall made of a second material that is different than the first material.

2. The system of claim 1, wherein the transition zone is a fused transition zone.

3. The system of claim 2, wherein the fused transition zone is a thermally fused transition zone.

4. The system of claim 1, further comprising:
a guidewire having a third flexural modulus along at least a portion of its length,
wherein the first flexural modulus is configured to increase a buckling force of the cannula and the second flexural modulus is less than or equal to the third flexural modulus.

5. The system of claim 1, wherein the distal opening is configured to be inserted in a right ventricle of a heart.

6. The system of claim 1, wherein the first distal section of the cannula includes a first distal inner wall made of a third material that is different than the first material, and a first distal outer wall made of a fourth material that is different than the second material and the third material.

7. The system of claim 1, wherein the first flexural modulus is equal to or greater than 23,000 psi, and the second flexural modulus is equal to or lower than 15,000 psi.

8. The system of claim 1, wherein the first flexural modulus is greater than 10,000 psi, and the second flexural modulus is smaller than 10,000 psi.

9. The system of claim 1, wherein the first distal section of the cannula includes a first distal inner wall made of the first material and a first distal outer wall made of a third material that is different than the second material.

10. The system of claim 1, wherein the cannula includes an inner wall and an outer wall and a reinforced coil located between the inner wall and the outer wall.

11. The system of claim 10, wherein at least a portion of the reinforced coil has a variable pitch length.

12. The system of claim 1, wherein a length of the proximal section is between 10%-50% of a length of the cannula.

13. The system of claim 1, wherein the cannula includes a second distal section between the first distal section and a distal end, and a second fused transition zone between the first distal section and the second distal section.

14. The system of claim 13, wherein the second distal section includes a second distal inner wall made of a third material and a second distal outer wall made of a fourth material, wherein a flexural modulus of the fourth material is greater than a flexural modulus of the third material.

15. The system of claim 13, wherein the second distal section includes a second distal inner wall made of the first material and a second distal outer wall made of a fourth material, wherein a flexural modulus of the fourth material is greater than a flexural modulus of the first material.

16. The system of claim 13, wherein a length of the second distal section is between 10-40% of a length of the cannula.

17. The system of claim 1, wherein each of the first and second curves forms an 'S' shape.

18. A cannula for inserting a percutaneous pump comprising an impeller, the cannula comprising:
a proximal opening configured to couple to the percutaneous pump;
a distal opening, wherein the percutaneous pump is configured to circulate blood through a bore of the cannula between the distal and proximal openings when the percutaneous pump is disposed in a vasculature of a patient;
a proximal section having a first flexural modulus that is constant along its length; and
a first distal section fused to the proximal section, the first distal section having a second flexural modulus that is constant along its length and which is smaller than the first flexural modulus,
wherein the proximal section forms a first curve in a first plane, and the first distal section forms a second curve in a second plane different from the first plane7 and wherein the proximal section of the cannula includes a proximal inner wall made of a first material and a proximal outer wall made of a second material that is different than the first material.

19. The cannula of claim 18, further comprising:
a guidewire having a third flexural modulus along at least a portion of its length,
wherein the first flexural modulus is configured to increase a buckling force of the cannula and the second flexural modulus is less than or equal to the third flexural modulus.

20. The cannula of claim 18, wherein a the distal opening of the cannula is configured to be inserted in a right ventricle of a heart.

21. The cannula of claim 18, wherein each of the first and second curves forms an 'S' shape.

* * * * *

UNITED STATES PATENT AND TRADEMARK OFFICE
CERTIFICATE OF CORRECTION

PATENT NO. : 10,849,653 B2
APPLICATION NO. : 15/419203
DATED : December 1, 2020
INVENTOR(S) : Zhenghong Tao et al.

Page 1 of 1

It is certified that error appears in the above-identified patent and that said Letters Patent is hereby corrected as shown below:

In the Claims

Column 18, Line 40, Claim 20, after "wherein" delete "a".

Signed and Sealed this
Sixteenth Day of March, 2021

Drew Hirshfeld
*Performing the Functions and Duties of the*
*Under Secretary of Commerce for Intellectual Property and*
*Director of the United States Patent and Trademark Office*